United States Patent [19]

Frei et al.

[11] Patent Number: 5,322,852

[45] Date of Patent: Jun. 21, 1994

[54] AMINOOXY PIPERIDINES AS ORNITHINE DECARBOXYLASE INHIBITORS

[75] Inventors: Jörg Frei, Hölstein; Jaroslav Stanek, Arlesheim, both of Switzerland

[73] Assignee: Ciba-Geigy Corp., Ardsley, N.Y.

[21] Appl. No.: 16,407

[22] Filed: Feb. 11, 1993

[30] Foreign Application Priority Data

Feb. 17, 1992 [CH] Switzerland .......................... 460/92

[51] Int. Cl.⁵ .................. A61K 31/445; C07D 211/40; C07D 211/26
[52] U.S. Cl. ..................................... 514/315; 546/242; 546/246
[58] Field of Search ................ 546/246, 242; 514/327, 514/331, 315

[56] References Cited

U.S. PATENT DOCUMENTS 5,086,051  2/1992  James et al. ....................... 514/228.2
5,169,867  12/1992  Stanek et al. ........................ 514/645

FOREIGN PATENT DOCUMENTS 0239309  9/1987  European Pat. Off. .
0369944  5/1990  European Pat. Off. .
0388309  9/1990  European Pat. Off. .
0452264  10/1991  European Pat. Off. .
0495750  7/1992  European Pat. Off. .
8918779  7/1990  South Africa .

OTHER PUBLICATIONS

Bell et al "Polyamines as intermediates in developmental neurotoxic events" CA 106:45043q (1987).
Bacchi. et al "Effects of the ornithine decarboxylase inhibitors. . . " CA 106:168537m (1987).
Breitenstein et al "EGME inhibits rat embryo ODC activity" CA 106:133263s (1987).
RN 112640-06-9, RN 96740-42-0 structure.
Chemical Abstracts 104:30840g. Khomutov et al. Aminooxy propylamine as an effective inhibitor of ornithine decarboxylase in vitro and in vivo. Bioorg. Khim. (1985).

Chemical Abstracts 108:131324e corresponding to FR 2,593,502. (1986).
Prabhu et al. "Synthesis and Structure-Activity Relationships of Selected Tricyclic Oxime O-Ethers as Potential Anticholinergic Agents". J. Pharm. Sci. 70, 558–562 (1981).
Grishina et al. "First Asymmetric Synthesis of 4-Piperidones. Preparation of Optically Active Diastereomers (List continued on next page.)

Primary Examiner—C. Warren Ivy
Assistant Examiner—Celia Chang
Attorney, Agent, or Firm—Irving M. Fishman; Karen G. Kaiser

[57] ABSTRACT

The invention relates to compounds of formula I

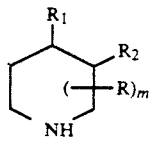

wherein either $R_1$ is a radical of formula Ia, $$—(CH_2)_n—O—NH_2 \quad \text{(Ia)}$$

in which n is 0 or 1, is hydrogen and $R_2$ is a radical of formula Ib, $$—(CH_2)_p—O—NH_2 \quad \text{(Ib)}$$

in which p is 1 or 2, and wherein R is $C_1$–$C_2$alkyl which is attached to one carbon atom of the central piperidine ring system, but not to the same carbon atom as $R_1$ of formula Ia or as $R_2$ of formula Ib; and m is 1 or 2, and salts thereof. The invention further relates to the preparation of these compounds, to intermediates obtained during their synthesis, to pharmaceutical compositions which contain them, and to the use of said compounds for the therapeutic treatment of the human or animal body and for the preparation of pharmaceutical compositions.

The compounds of formula I are inhibitors of ornithin decarboxylase.

11 Claims, No Drawings

OTHER PUBLICATIONS of 1-α-Phenylethyl-2-methyl-4-Piperidone". Chem. Het. Comp. 21, pp. 1132-1136 (1985).

Mistryukov. "Effect of Electrostatic Factors on the Stereochemistry of the Hydride Reduction of Ketones of the Piperidine Series". Bull. Acad. Sci. USSR Div. Chim. Sci. (Eng) 965, pp. 1788-1796 (1965).

Hodjat et al. "Aminomercuration X-Synthese D'Heterocycliques Monospiranniques par Aminomercuration Intramoléculaire". J. Heterocycl. Chem. 9, pp. 1081-1086 1972.

Casy et al. "Synthesis and Stereochemistry of Diastereoisomeric 1,3-Dimethylpiperidin-4-ols and Related Compounds". Can. J. Chem, 50, pp. 803-809 (1972).

LeBel et al. "Stereospecific Synthesis of 2,3,6-Trisubstituted Piperidines: An Efficient Total Synthesis of (≠)-Pumiliotoxin C". J. Am. Chem. Soc. 111, pp. 3363-3368 (1989).

Nazarov et al. "Heterocyclic Compounds. Communication XXIX. Stereoisomerism of 2,5-Dimethyl-4-Piperidinol, 1,2,5-trimethyl-4-piperidinol, and their derivatives". Bull. Acad. Sci. USSR, Div. Chim. Sci. (English), 1954, pp. 65-76 (1954).

Chemical Abstracts 57:2183d, corresponding to Chizhov, "ZH. Obshch. Khim." 31, pp 3469-3477 (1961).

Campbell et al. "Studies on γ-Pyrones, II. Synthesis of 4-Piperidinols from Pyrones". J. Org. Chem. 15, pp. 337-342 (1950).

Grochowski et al. "A New Synthesis of O-Alkylhydroxylamines". Synthesis 1976, pp. 682-684 (1976).

Pankanskie et al. "An Improved Synthetic Route to Aminoxypropylamine (APA) and Related Homologs". Synthetic Commun. 19, pp. 339-344 (1989).

AMINOOXY PIPERIDINES AS ORNITHINE DECARBOXYLASE INHIBITORS

The present invention relates to compounds of formula I

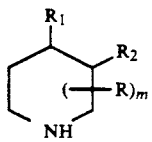
(I)

wherein either $R_1$ is a radical of formula Ia, $$-(CH_2)_n-O-NH_2 \qquad (Ia)$$

in which n is 0 or 1, and $R_2$ is hydrogen, or $R_1$ is hydrogen and $R_2$ is a radical of formula Ib, $$-(CH_2)_p-O-NH_2 \qquad (Ib)$$

in which p is 1 or 2, and wherein R is $C_1$–$C_2$alkyl which is attached to a carbon atom of the central piperidine ring system, but not to the same carbon atom as $R_1$ of formula Ia or as $R_2$ of formula Ib; and m is 1 or 2, and salts thereof. The invention further relates to the preparation of these compounds, to intermediates obtained during their synthesis, to pharmaceutical compositions which contain them, and to the use of said compounds for the therapeutic treatment of the human or animal body, and for the preparation of pharmaceutical compositions.

The substituents $R_1$ or $R_2$ as well as the substituents R may be on the same side or, independently of each other, on different sides with respect to the plane of the central piperidine ring system of the compounds of formula I, so that different isomers (diastereoisomers, enantiomers) or mixtures of isomers are conceivable. All substituents R are preferably located on one side with respect to the plane of the ring, whereas the substituent $R_1$ or $R_2$ is in trans-or cis-position relative to the substituents R, most preferably in trans-position.

Where there are centres of asymmetry, these may independently of one another be in the R-, S- or R,S-configuration. Those compounds of this invention which carry at least one asymmetrical carbon atom may preferably be in the form of pure enantiomers or of mixtures of enantiomers (racemates).

The symbols and general terms used in the description of this specification preferably have the following meanings.

When $R_1$ is a radical of formula Ia, n is 0 or 1, preferably 0.

When $R_2$ is a radical of formula Ib, p is 1 or 2, preferably 1.

When m is 2, the substituents R may each independently of the other be $C_1$–$C_2$alkyl, typically methyl or ethyl. In that case, those compounds are preferred in which all substituents R are identical (either all methyl or all ethyl).

A substituent R is not bonded to the same carbon atom as either a substituent $R_1$ of formula Ia (i.e. $R_1$ is not hydrogen) or a substituent $R_2$ of formula Ib (i.e. $R_2$ is not hydrogen).

Salts of novel compounds are in particular pharmaceutically acceptable acid addition salts, i.e. those acid addition salts that do not have perceptible toxicity in the contemplated doses, typically salts with inorganic acids such as hydrochloric acid, sulfuric acid or phosphoric acid, or with suitable organic carboxylic or sulfonic acids, typically acetic acid, octanoic acid, succinic acid, adipic acid, fumaric acid, maleic acid, hydroxymaleic acid, propionic acid, lactic acid, malic acid, citric acid, salicylic acid, p-aminosalicyclic acid, ascorbic acid, oxalic acid, benzenesulfonic acid, 1,5-naphthalenedisulfonic acid, methanesulfonic acid or 1,2-ethanedisulfonic acid, with N-cyclohexylsulfamic acid or, conveniently, with amino acids such as glutamic acid or aspartic acid. Monobasic or dibasic salts may be formed, depending on the number and basicity of the basic groups present.

Pharmaceutically unsuitable salts, for example picrates or perchlorates, may be used in addition for isolating or purifying the novel compounds. Only the pharmaceutically acceptable salts are suitable for therapeutic use and for this reason are preferred.

The novel compounds have useful, especially pharmacologically useful, properties. Surprisingly, it has been found that the compounds of formula I have in particular a pronounced specific inhibitory action on the ornithin decarboxylase (ODC) enzyme. They therefore constitute a novel class of ODC inhibitors.

As key enzyme, ODC plays an important part in polyamine biosynthesis, which occurs in virtually all cells of mammals, including humans. ODC regulates the polyamine concentration in the cell. Inhibition of the ODC enzyme leads to a reduction of the polyamine concentration. As a reduction of the polyamine concentration inhibits cell growth, it is possible by administering ODC inhibiting substances to inhibit the growth of eucaryotic and also of procaryotic cells, especially of cells that grow rapidly or uncontrollably, and even to kill cells or to inhibit the onset of cell differentiation.

The inhibition of the ODC enzyme can be demonstrated by means of, inter alia, the method of J. E. Seely and A. E. Pegg, Ornithin Decarboxylase (Mouse Kidney), pages 158-161, in H. Tabor and C. White-Tabor (Eds.): Methods in Enzymology, Vol. 94: Polyamines, Academic Press, New York 1983. By using in this test ODC from rat liver (isolation: Hayashi, S.-I. and Kameji, T., op. cit. pages 154-158), $IC_{50}$ values are obtained for the compounds of formula I in the micromolar range down to about 0.2 µM, from about 0.2 to 20 µM, e.g. from 0.21 to 6.1 µM. $IC_{50}$ is the concentration of the inhibitor at which the ODC activity is 50% of a control without inhibitor.

As ODC inhibitors the compounds of formula I have antiproliferative properties, which can be demonstrated, inter alia, by showing the inhibitory action on the growth of human T24 bladder carcinoma cells. Proof is adduced by incubating these cells in "Eagle's minimal essential medium", to which 5% (v/v) of foetal calf serum is added, in a humidified incubator at 37° C. and 5 percent by volume of $CO_2$ in air. The carcinoma cells (1000–1500) are inoculated into 96-well microtiter plates and incubated overnight under the stated conditions. The test substance is added in serial dilutions on day 1. The plates are incubated under the stated conditions for 5 days. During this time, the control cultures undergo at least 4 cell divisions. After the incubation, the cells are fixed with 3.3% (weight/volume=w/v) of an aqueous solution of glutaraldehyde, washed with water and stained with a 0.05% (w/v) aqueous solution of methylene blue. After washing, the dye is eluted with 3% (w/v) of aqueous hydrochloric acid. Afterwards, the optical density (OD) per hole which is directly proportional to the number of cells, is measured with a photometer (Titertek multiskan) at 665 nm. The $IC_{50}$ values are computed by a computer system using the formula $$IC_{50} = \frac{OD_{665}(test) - OD_{665}(start)}{OD_{665}(control) - OD_{665}(start)} \times 100.$$

The $IC_{50}$ values are defined as that active compound concentration at which the number of cells per hole at the conclusion of the incubation time is only 50% of the number of cells in the control cultures.

The compounds of formula I are thus particularly suitable for the treatment of conditions that respond to an inhibition of ornithin decarboxylase, for example benign and malignant tumours. They are able to effect tumour regression and, furthermore, to prevent the spread of tumour cells as well as the growth of micrometastases. In addition, they are suitable for the treatment of protozoa infections, including trypanosomiasis, malaria or pneumonia caused by Pneumocystis carinii.

As selective ODC inhibitors, the compounds of formula I can be used by themselves or also in conjunction with other pharmacologically active substances. Contemplated is, inter alia, a combination with (a) inhibitors of other enzymes of polyamine biosynthesis, typically S-adenosylmethionine decarboxylase inhibitors, (b) inhibitors of proteinkinase C, (c) inhibitors of tyrosine proteinkinase, (d) cytokines, (e) negative growth regulators, (f) aromatase inhibitors, (g) antioestrogens or (h) classical cytostatic compounds.

Preferably the invention relates to compounds of formula I wherein R is bonded only to that ring carbon atom which is bound direct to the nitrogen hetero atom of the central piperidine ring system, and the other symbols are as defined above, and salts thereof.

Preferred are also compounds of formula I, wherein either n is 0 when the substituent $R_1$ is defined by the radical of formula Ia, or wherein p is 1 when the substituent $R_2$ is defined by the radical of formula Ib, and the other symbols have the meanings mentioned above, and salts thereof.

Those compounds of formula I are very preferred in which n is 0 when $R_1$ is defined as the radical of formula Ia, or p is 1 when $R_2$ is defined as the radical of formula Ib, and the other symbols are as defined above, with the proviso that R is bonded only to that ring carbon atom which is attached direct to the nitrogen hetero atom of the central piperidine ring system, and, preferably pharmaceutically acceptable, salts thereof.

To be singled out for special mention are compounds of formula II

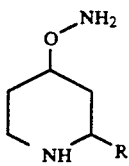

(II)

wherein R is $C_1$–$C_2$alkyl, and pharmaceutically acceptable salts thereof.

Among these compounds of formula II, those compounds merit very special interest in which the —O—$NH_2$ radical and the substituent R which is $C_1$–$C_2$alkyl, i.e. methyl or ethyl, are bonded in trans-position relative to each other to the central piperidine ring system, and pharmaceutically acceptable salts thereof.

The most preferred compound of formula II is that wherein R is methyl and is bonded to the central piperidine ring system in trans-position relative to the —O—$NH_2$ radical, or a pharmaceutically acceptable salt thereof.

Compounds of special interest are also compounds of formula III

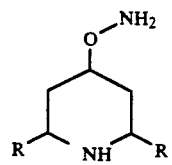

(III)

wherein the substituents R are each independently of the other $C_1$–$C_2$alkyl, and pharmaceutically acceptable salts thereof.

Very particularly preferred is the compound of formula III, wherein R is methyl and both substituents R are bonded to the central piperidine ring system in cis-position relative to each other, but in trans-position relative to the —O—$NH_2$ radical, or a pharmaceutically acceptable salt thereof.

The invention relates most particularly to the specific compounds described in the Examples and pharmaceutically acceptable salts thereof.

The novel compounds and their salts can be prepared by processes which are known per se, typically by (a) removing the amino protective group or groups from a compound of formula I, wherein at least one amino group is protected, preferably from a compound of formula IV

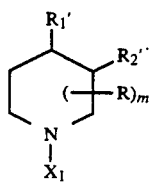

(IV)

or a salt thereof, provided salt-forming groups are present, wherein either $R_1'$ is a radical of formula IVa,

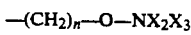

—$(CH_2)_n$—O—$NX_2X_3$    (IVa)

wherein n is 0 or 1, and $R_2'$ is hydrogen, or $R_1'$ is hydrogen and $R_2'$ is a radical of formula IVb,

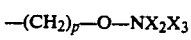

—$(CH_2)_p$—O—$NX_2X_3$    (IVb)

wherein p is 1 or 2, and the other symbols are as defined for the compounds of formula I, and $X_1$, $X_2$ and $X_3$ are each independently of one another an amino protective group or hydrogen, with the proviso that at least one of said groups $X_1$, $X_2$ and $X_3$ is an amino protective group, or wherein $X_1$ is an amino protective group or hydrogen, and $X_2$ and $X_3$ together form a bivalent amino protective group, or (b) reacting a compound of formula V

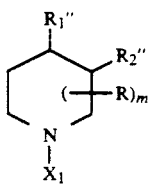

or a salt thereof, provided salt-forming groups are present, wherein $X_1$ is hydrogen or an amino protective group; either $R_1''$ is a radical of formula Va, $$-(CH_2)_n-W_1 \qquad (Va)$$

wherein $W_1$ is a leaving group, and n is 0 or 1, and $R_2''$ is hydrogen; or $R_1''$ is hydrogen and $R_2''$ is a radical of formula Vb $$-(CH_2)_p-W_2 \qquad (Vb)$$

wherein $W_2$ is a leaving group, and p is 1 or 2; and the other symbols are as defined for the compounds of formula I, with an amino-protected hydroxylamine derivative under substitution of either $W_1$ or $W_2$, further functional groups in the starting materials which shall not participate in the reaction being in protected form, and removing protective groups present, and, if desired, converting a compound of formula I into another compound of formula I, resolving a mixture of isomers into the individual isomer, and/or converting a free compound of formula I into a salt or a salt into the free compound of formula I or into another salt.

Within the scope of this invention, the qualifying prefix "lower" denotes a radical containing 1 to 7, preferably 1 to 4, carbon atoms. Lower alkyl is typically methyl, ethyl, propyl, butyl, pentyl, hexyl, heptyl. An alkyl radical of 3 to 7 carbon atoms may be straight-chain or branched and is typically isopropyl, isobutyl, sec-butyl, tert-butyl, isopentyl or neopentyl.

Alkyl denotes a saturated, branched or unbranched hydrocarbon radical containing up to 20, preferably up to 12, carbon atoms and is typically dodecyl, undecyl, decyl, nonyl, octyl or, preferably, lower alkyl.

Aryl preferably contains up to 14 carbon atoms and is preferably phenyl which is substituted by one or more than one member, preferably by one, two or three members, selected from the group consisting of lower alkyl, preferably methyl, tert-lower alkyl such as tert-butyl, lower alkoxy such as methoxy, hydroxy, halogen such as fluoro, chloro, bromo or iodo and/or nitro, or is naphthyl or 9-fluorenyl, and is most preferably unsubstituted or substituted phenyl.

Process (a): Preferred monovalent amino protective groups $X_1$, $X_2$ and $X_3$ are acyl groups, preferably lower alkanoyl such as formyl, acetyl or propionyl, halo-lower alkanoyl such as 2-haloacetyl, preferably 2-chloroacetyl, 2-bromoacetyl, 2-iodoacetyl, 2,2,2-trifluoroacetyl or 2,2,2-trichloroacetyl, unsubstituted benzoyl or benzoyl which is substituted by halogen, lower alkoxy, lower alkoxycarbonyl or nitro, e.g. benzoyl, 4-chlorobenzoyl, 4-methoxybenzoyl, 2-methoxycarbonylbenzoyl or 4-nitrobenzoyl, the acyl radical of carbonic acid half-ester, especially arylmethoxycarbonyl containing one or two aryl radicals which preferably represent phenyl or phenyl which is substituted by one or more than one member selected from the group consisting of lower alkyl, preferably tert-lower alkyl such as tert-butyl, lower alkoxy, e.g. methoxy, hydroxy, halogen, e.g. chloro and/or nitro, or naphthyl or 9-fluorenyl, e.g. unsubstituted or substituted benzyloxycarbonyl, e.g. 4-nitrobenzyloxycarbonyl, or substituted diphenylmethoxycarbonyl, e.g. bis(4-methoxyphenyl) methoxycarbonyl, 2-halo-lower alkoxycarbonyl, e.g. 2,2,2-trichloroethoxycarbonyl, 2-bromomethoxycarbonyl or 2-iodoethoxycarbonyl, lower alkoxycarbonyl, preferably lower alkoxycarbonyl which is branched in 1-position of the lower alkyl moiety or suitably substituted in 1- or 2-position, preferably tert-lower alkoxycarbonyl, e.g. tert-butoxycarbonyl, alkylformimidoyl such as lower alkylformimidoyl, e.g. tert-butylformimidoyl, or arylmethyl groups such as mono-, di- or, preferably, triarylmethyl, in which the aryl moieties are preferably unsubstituted or substituted phenyl radicals, e.g. benzyl, diphenylmethyl or triphenylmethyl (trityl).

Especially preferred monovalent amino protective groups $X_1$, $X_2$ and $X_3$ are acyl radicals of carbonic acid half-esters, preferably lower alkoxycarbonyl, e.g. tert-butoxycarbonyl, unsubstituted benzyloxycarbonyl or benzyloxycarbonyl which is substituted as indicated above, typically 4-nitrobenzyloxycarbonyl, diphenylmethoxycarbonyl or 2-halo-lower alkoxycarbonyl, e.g. 2,2,2-trichloroethoxycarbonyl, also trityl, formyl or 2-methoxy-carbonylbenzoyl, or lower alkylformimidoyl radicals, preferably those in which the lower alkyl moiety is mono- or dibranched in 1-position, e.g. tert-butylformimidoyl. The most preferred meaning of $X_1$ is lower alkoxycarbonyl, e.g. tert-butoxycarbonyl.

Preferred bivalent amino protective groups formed from the radicals $X_2$ and $X_3$ are mono-or disubstituted methylidene groups, e.g. 1-lower alkoxy (preferably methoxy or ethoxy)-lower alkylidene (typically methoxy- or ethoxyethylidene or methoxy- or ethoxy-1-n-butylidene), e.g. $=C(CH_3)(OC_2H_5)$, also e.g. $=C(CH_3)_2$ or $=CH$-phenyl, and preferably bisacyl radicals which are bonded through both carbonyl groups, preferably unsubstituted phthalyl or phthalyl which carries the same substituents as defined above for substituted benzoyl, conveniently the phthalyl radical which, together with the nitrogen atom to be protected, forms 1H-isoindol-1,3(2H)-dione (phthalimido group), or lower alkyldicarboxylic acid radicals, e.g. the succinic acid radical, lower alkenyldicarboxylic acid radicals, e.g. the maleic acid radical, or $C_6$–$C_{12}$bicyclodicarboxylic acid radicals, e.g. the 5-norbornene-2,3-dicarboxylic acid radical.

Amino protective groups, their introduction and their removal are known per se and described, inter alia, in J. F. W. McOmie, "Protective Groups in Organic Chemistry", Plenum Press, London, New York, 1973, and T. W. Greene, "Protective Groups in Organic Synthesis", Wiley, N.Y., 1984. The introduction of alkylformimidoyl radicals is described, inter alia, by Meyers, A. et al., in J. Am. Chem. Soc. 106, 3270 (1984); the tert-butylformimidoyl radical is introduced typically by reacting the free amino compound with N,N-dimethyl-N'-butylformamidine in the presence of a catalytic amount of ammonium sulfate in toluene at reflux temperature or, alternatively, by reacting tert-butylformamide with $Et_3O^+$ $BF_4^-$ in methylene chloride at room temperature, addition of the amino compound and by further reaction in the temperature range from room temperature to 40° C.

The removal of the amino protective groups is carried out stepwise or simultaneously, depending on the kind of protective group or groups in a manner known per se, conveniently by reduction or solvolysis, preferably hydrolysis, preferably in acid medium, alcoholysis, acidolysis or hydrazinolysis. Lower alkoxycarbonyl, e.g. the tert-butoxycarbonyl group, or the trityl group, can be set free typically by treatment with an acid, e.g. a mineral acid such as a hydrohalic acid, typically hydrochloric acid, in the presence or absence of a solvent, especially methanol or tetrahydrofuran, or an inorganic acid such as formic acid, acetic acid or trifluoroacetic acid, in the presence or absence of water or an organic solvent such as methylene chloride. The removal of the unsubstituted or substituted benzyloxycarbonyl group is conveniently effected reductively by hydrogenolysis, i.e. by treatment with hydrogen in the presence of a suitable catalyst, e.g. palladium, or with sodium in liquid ammonia, or by acidolysis, preferably with hydrobromic acid/glacial acetic acid. 2-Halo-lower alkoxycarbonyl can be split off by treatment with a suitable reducing agent such as zinc in the presence of an organic solvent, typically methanol or aqueous acetic acid. The removal of lower alkylformimidoyl, e.g. tert-butylformimidoyl, is preferably effected with a base, conveniently a hydroxide, preferably an alkali metal hydroxide such as potassium hydroxide. The removal of bisacyl radicals, especially the phthalyl group, may be effected with hydrazine hydrate or with an acid, preferably a mineral acid, e.g. a hydrohalic acid such as hydrochloric acid, in the presence or absence of an organic solvent, e.g. an alcohol such as methanol.

Process (b): In a compound of formula V, a substituent $W_1$ (Va) or $W_2$ (Vb) is a leaving group, preferably a derivatised hydroxy group, e.g. sulfonyloxy substituted by aliphatic or aromatic groups, typically lower alkanesulfonyloxy, such as methanesulfonyloxy, or lower alkylphenylsulfonyloxy (=lower alkylphenyl-$SO_2$—O—) such as p-toluenesulfonyloxy, a derivatised sulfonyl group such as halo-lower alkanesulfonyl, e.g. trifluoromethanesulfonyl or, in particular, a free hydroxy group or a halogen atom, e.g. a chlorine, bromine or iodine atom.

Where $W_1$ or $W_2$ are hydroxy, the reaction is preferably carried out by an intramolecular dehydration reaction. A particularly preferred reaction is a variant of the Mitsunobu reaction (q.v. Synthesis, 682 (1976)), wherein the compound of formula V is reacted with an amino-protected hydroxylamine derivative in which the amino function is protected by one of the bivalent amino protective groups mentioned in connection with process (a), e.g. N-hydroxyphthalimide, N-hydroxy-5-norbornene-2,3-dicarboximide or ethyl acethydroxamate, preferably N-hydroxyphthalimide, and triarylphosphine, e.g. triphenylphosphine, and a diester of N,N'-azodicarboxylic acid, e.g. a di-lower alkyl ester of N,N'-azodicarboxylic acid, conveniently diethyl N,N'-azodicarboxylate, preferably in an aprotic solvent such as an ether, e.g. a cyclic ether such as tetrahydrofuran, or preferably an aromatic solvent such as benzene or toluene, preferably under inert gas such as nitrogen, and in the preferred temperature range from 0° C. to 80° C., more particularly from 10° to 40° C,. typically from 20° to 30° C. This reaction is preferably carried out such that inversion occurs at the carbon atom carrying the hydroxy group.

The reaction results in a group of formula —O—$NH_2$ as $R_1'$ or $R_2'$ in a compound of formula IVa, which group is protected by a bivalent amino protective group, especially a bisacyl radical, and which can be set free as described in process (a), preferably by hydrolysis, especially in aqueous solution in the presence of an acid, preferably a mineral acid, e.g. a hydrohalic acid such as hydrochloric acid, in the presence or absence of an organic solvent, e.g. an alcohol such as methanol, in the temperature range from room temperature to the reflux temperature of the reaction mixture, preferably from 80° C. to reflux temperature, e.g. at reflux temperature.

If $W_1$ or $W_2$ is a derivatised hydroxyl group or, preferably, a halogen atom, e.g. a bromine atom, then the reaction is preferably carried out with an amino-protected hydroxylamine derivative (as in Synthetic Communications 19, 339 (1989)), preferably a hydroxamic acid such as benzoylhydroxamic acid, in an aprotic solvent, preferably a carboxamide such as a N,N-di-lower alkyl-lower alkanoylamide, e.g. formamide, with the addition of an alcoholate, conveniently an alkali metal lower alkyl oxide, typically sodium methoxide, in the temperature range from 0° to 80° C., preferably from 30° to 40° C., typically at room temperature, in the presence or absence of an inert gas such as nitrogen.

This reaction gives a group of formula —O—$NH_2$ as $R_1'$ or $R_2'$ in a compound of formula IV, which group is protected by an amino protective group, especially an unsubstituted or substituted benzoyl radical, as defined in connection with process (a), and which can be set free as described in process (a), preferably as just described above for —O—$NH_2$ protected by a bivalent protective group.

Further functional groups in starting materials which shall not participate in the conversion are mainly primary and secondary amino groups and can be protected by suitable protective groups (conventional protective groups), preferably by amino protective groups (as in a compound of formula V protected by an amino protective group as $X_1$ at the piperidine nitrogen), as described above in process (a).

The removal of protective groups, especially the liberating of the protected amino groups after the conversion of $W_1$ or $W_2$, is preferably effected as described in process (a).

Additional process measures

The conversion of a compound of formula I into another compound can, for example, be carried out by introducing a further substituent R into a compound of formula I in which there is only one substituent R. Thus a compound of formula II, wherein the substituents have the given meanings, can be converted into a compound of formula III by initially introducing amino protective groups as described in process (a), in which case an acyl radical of a carbonic acid half-ester, e.g. tert-lower alkoxycarbonyl, preferably tert-butoxycarbonyl, or a lower alkylformimidoyl radical such as tert-butylformimidoyl, is especially preferred as protective group at the piperidine nitrogen atom. Subsequent reaction is carried out with a lower alkyllithium compound, e.g. tert-butyllithium, which is dissolved in a cyclic linear or branched hydrocarbon or a mixture of such hydrocarbons, e.g. cyclohexane:isopentane, in the presence of a tertiary nitrogen base such as N,N,N',N'-tetramethylethylenediamine in an aprotic solvent, e.g. an ether such as dimethyl ether, tetrahydrofuran or a mixture thereof, in the temperature range from −100° to −20° C., preferably from about −60° to about −75° C., to give a derivative of the protected compound of formula I, which is lithiated at the ring carbon atom adjacent to the ring carbon atom of the piperidine ring system. This derivative is then preferably further processed immediately in situ by reaction with a strongly electrophilic methyl or ethyl derivative, e.g. methyl or ethyl iodide, dimethyl sulfate or diethyl sulfate, in an aprotic solvent as just defined, and in the temperature range just mentioned. The compound of formula III is then obtained by setting free the amino groups as described in process (a).

Mixtures of isomers of compounds of formula I, which may be obtained in the form of several isomers, can be separated by per se known methods into the individual isomers or into mixtures of isomers, e.g. diastereoisomers (e.g. with respect to the cis-or trans-position of substituents), racemates or enantiomers.

Mixtures of diastereoisomers can be separated into individual diastereoisomers, preferably by chromatographic methods, typically by distribution or adsorption chromatography, or by distribution into multiphase solvent mixtures.

Mixtures of enantiomers can conveniently be separated into individual enantiomers, preferably by forming salts with optically pure salt-forming reagents and separating the mixture of diastereoisomers so obtained, conveniently by fractional crystallisation or by chromatography on optically active column materials.

Further, it is possible to prepare from compounds of formula I compounds of formula IV for purification purposes. The liberation of the purified compounds of formula I is then effected by removal of protective groups as described in process (a).

Depending on the mode of carrying out the reaction or on the reaction conditions, the novel compounds containing salt-forming basic groups can be obtained in the free form or in the form of salts.

The compounds, including their salts, can also be obtained in the form of their hydrates, or their crystals may include the solvent used for crystallisation.

Salts of free compounds of formula I can be prepared in per se known manner, typically by treatment with an acid, e.g. an inorganic acid such as hydrochloric acid or sulfuric acid, an organic carboxylic acid such as adipic acid, or an organic sulfonic acid such as benzenesulfonic acid, or a suitable anion exchange reagent which is charged with the anion of the appropriate acid. Salts can be converted in conventional manner into the free compounds, typically by treatment with a suitable base, e.g. a hydroxy base in free solution, typically an alkali metal hydroxide, or with an anion exchanger charged with hydroxide, e.g. by chromatography or in a batch process.

The conversion of a salt of a compound of formula I can be carried out via the synthesis of the free compound and the subsequent reaction thereof to give an acid addition salt, as just described.

The direct conversion of an acid addition salt of one of the compounds of formula I and an acid with another acid into an acid addition salt of the compound of formula I and the second, new acid is also possible. This conversion is preferably carried out a) by reacting the original acid addition salt in free solution in the presence of a suitable amount of the new acid, e.g. an excess, or b) at an anion exchanger charged with the anion of the new acid.

Gel chromatographic ion exchange methods can also be used for all reactions which are suitable for the conversion of acid addition salts of bases of formula I into other acid addition salts or into the free compounds, or of the free bases into the corresponding acids.

The conversion of a salt, preferably of a halide, e.g. a chloride, into another salt, typically a salt of an acid carrying two negative charges, e.g. a sulfate, is especially preferred whenever a crystalline salt of a compound of formula I is obtained.

Starting materials

The starting materials of formula V are known or they are prepared by per se known methods.

For example, they may be obtained (A) by hydrogenation of suitably substituted pyridines of formula VI

(VI)

wherein the substituents are as defined for compounds of formula V, preferably with hydrogen in the presence of a catalyst, preferably a Pt-Pd mixed bed catalyst in a carboxylic anhydride such as acetic anhydride, a rhodium/carbon catalyst in an alcohol such as ethanol, a platinum, rhodium, palladium, nickel, ruthenium catalyst, nickel on silicate carriers, Raney nickel or a palladium/carbon catalyst, under atmospheric or elevated pressure. Representative examples of a compound of formula VI are 3,5-dimethyl- or 3,5-diethyl-4-hydroxypyridine, which is obtained by heating suitably substituted bipyridylium salts with phosphoric acid (Synthesis, 454 (1979)), 3-methyl-4-hydroxypyridine, which is obtained by heating 3-methyl-4-pyridylamine in aqueous sulfuric acid and aqueous sodium nitrite via the diazonium salt (Archiv der Pharmazie 290, 494, 509 (1957)), or by heating 4-hydroxy-5-methylnicotinic acid under decarboxylation (op. cit. p. 508), and 2,3-dimethyl-4-hydroxypyridine, which is obtained from 2,3-dimethyl-4-nitropyridine with potassium acetate in acetic anhydride at reflux temperature and subsequent hydrolysis of the resultant 4-acetoxy-2,3-dimethoxypyridine (J. Org. Chem. 44, 870 (1979); or (B) provided the compounds of formula V are those which in 4-position contain a hydroxyl group as $R_1''$ and hydrogen as $R_2''$, they can be obtained from suitably substituted γ-pyrones of formula VII,

(VII)

wherein R and m are as defined for compounds of formula I, such that they are first converted in the presence of ammonia in an alcohol such as ethanol (J. Chem. Soc., 3023 (1931)), into the corresponding γ-pyridones, and subsequently hydrogenated to give the corresponding 4-hydroxypiperidines of formula V, for example as described in (A) above in respect of the pyridines, or converted direct by reduction in the presence of ammonia, conveniently with sodium, or by hydrogenation in the presence of platinum or palladium into 4-hydroxypiperidines. Typical examples of compounds of formula VII are 2,6-dimethyl-γ-pyrone, which can be prepared from dehydroacetic acid (Bull. Chem. Soc. Japan 48, 508 (1975), 2,6-diethyl-γ-pyrone, formed by heating 6-ethyl-3-propionylpyran-2,4-dione with aqueous hydrochloric acid (J. Indian Chem. Soc. 9, 303, 305 (1932)), 2-methyl-3-ethyl-γ-pyrone and 2,3-dimethyl-γ-pyrone, which are conveniently prepared by heating 3-ethyl- or 3-methyl-2,4-pentandione in ethylene glycol and with p-toluenesulfonic acid as catalyst to reflux temperature via the corresponding ketal (3-ethyl- or 3-methyl-4,4-(ethylenedioxy)pentan-2-one), which is then acetylated at room temperature in the presence of diethyl oxalate and sodium methoxide in anhydrous methanol to ethyl-2,4-diketo-5-ethyl- or -methyl-6,6-(ethylenedioxy)heptanoate, which is hydrolysed in an aqueous solution of hydrochloric acid to give 2-methyl-3-ethyl- or 2,3-dimethyl-4-pyrone-6-carboxylic acid, which is then decarboxylated by heating to 240° C. with copper powder under atmospheric pressure to give the cited pyrones (J. Org. Chem. 49, 4523 (1984), or 3-methyl-γ-pyrone, which may conveniently be obtained from the potassium salt of the monomethyl ether of bisoxymethylene acetone in methanolic solution and methyl iodide (Willstätter and Pummerer, Chemische Berichte 38, 1461 (1905); or they can be prepared (C) by cyclisation of compounds of formula VIII,

wherein L is a nucleofugic leaving group, typically one of those mentioned above in the definition of $W_1$ and $W_2$ in process (b), preferably an amino group, and the other substituents are as defined for the compounds of formula V, such that if an amino group L is present, said group and the further amino group are preferably in protonated form, conveniently as salt of a hydrohalic acid such as hydrochloric acid, and the reaction is carried out by heating; or (D) provided the compounds of formula V are those containing in 4-position a hydroxyl group as substituent $R_1''$ and hydrogen as $R_2''$, they can be obtained by cyclisation of compounds of formula IX,

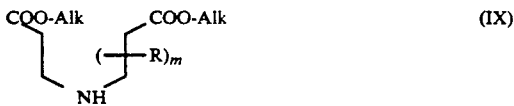

wherein Alk is lower alkyl, preferably methyl or ethyl, and the other substituents are as defined for the compounds of formula I, by base catalysis in general accordance with the Dieckmann method and subsequent hydrolysis and decarboxylation to give the corresponding 4-piperidones (q.v. inter alia J. Am. Chem. Soc. 51, 924 (1929); J. Am. Chem. Soc. 70, 1820, 1826 (1948), which are then hydrogenated to the 4-hydroxypiperidines of formula V, conveniently under the hydrogenation conditions described in (A), or with complex hydrides, typically sodium borohydride in alcoholic solution, e.g. methanol, or with sodium in an absolute alcohol such as ethanol; or (E) provided the compounds of formula V are those wherein $R_1''$ is hydroxy and $R_2''$ is hydrogen, m is 2 and both substituents R are bonded to the two carbon atoms adjacent to the nitrogen and both substituents R are identical, they can be synthesised by cyclisation of 2 mol of acetaldehyde or propionaldehyde, 1 mol of an acetonedicarboxylic acid ester and ammonia or a primary amine in accordance with the method of Petrenko-Kritschenko, to give 4-piperidones, which can then be converted under hydrogenation conditions as described in (A), or with complex hydrides, typically sodium borohydride, in alcoholic, e.g. methanolic, solution, or with sodium in an absolute alcohol such as ethanol, into the corresponding 4-hydroxy compounds; or they can be obtained (F) by a process analogous to the Hantzsch pyridine synthesis by condensation of 2 mol of a suitably substituted β-dicarbonyl compound with 1 mol of an aldehyde in the presence of ammonia to give the corresponding dihydropyridine derivatives, and subsequent oxidation of these compounds to the corresponding pyridine derivatives and decarboxylation, conveniently by hydrolysing the esters and heating, and, finally, hydrogenating the resultant substituted pyridines, as described in (A); or (G) provided the compounds of formula V are those wherein R is not bonded to a carbon atom adjacent to the ring nitrogen atom of the piperidine ring system, they can be obtained by reaction of 1,5-dicarbonyl compounds of formula X

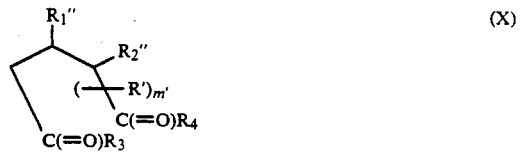

wherein $R_1''$ and $R_2''$ are defined for compounds of formula I, $R_3$ and $R_4$ are each independently of the other hydrogen, methyl or ethyl, R' is methyl or ethyl and is not bonded direct to one of the carbonyl carbon atoms, and m' is 0, 1 or 2, with the proviso that m' is 0 if both substituents $R_3$ and $R_4$ have a meaning different from hydrogen, or m' is 0 or 1 if only one of the substituents $R_3$ or $R_4$ has a meaning different from hydrogen, or m' is 1 or 2 if both substituents $R_3$ and $R_4$ are hydrogen, conveniently by subjecting these compounds to cyclisation by hydrogenation in the presence of ammonia (1,5-dialdehydes are the preferred starting materials ($R_3=R_4=H$)). For example, 3-(2-hydroxyethyl)piperidine can be prepared from 2-hydroxyethylglutaraldehyde by hydrogenation in the presence of Raney nickel, hydrogen and ammonia (Bulletin de la Société Chimique de France, page 1139 (1954)), into which methyl or ethyl groups in 2- or 6-position can then be introduced, as described in the conversion of compounds of formula II into those of formula III; or (H) provided the compounds of formula V are those wherein n is 1 in the definition of $R_1$ as the radical of formula Ia, or p is 1 or 2 in the definition of $R_2$ as the radical of formula Vb, they can be obtained by reduction of esters of formula XI,

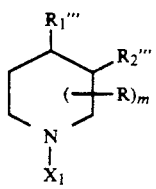

(XI)

wherein either R₁'" is an esterified carboxyl group, preferably an alkoxycarbonyl, aryloxycarbonyl or aryl-lower alkoxycarbonyl group, e.g. lower alkoxycarbonyl such as methoxycarbonyl, ethoxycarbonyl or n-butoxycarbonyl, 4-nitrophenoxycarbonyl or benzyloxycarbonyl, and R₂'" is a hydrogen atom, or R₁'" is a hydrogen atom and R₂'" is an esterified carboxyl group or an esterified carboxymethyl group, preferably an alkoxycarbonyl, aryloxycarbonyl or aryl-lower alkoxycarbonyl group or an alkoxycarbonylmethyl, aryloxycarbonylmethyl or aryl-lower alkoxycarbonylmethyl group, e.g. lower alkoxycarbonyl such as methoxycarbonyl, ethoxycarbonyl or n-butoxycarbonyl, or lower alkoxycarbonylmethyl such as methoxycarbonylmethyl, ethoxycarbonylmethyl or n-butoxycarbonylmethyl, and the other substituents are as defined for the compounds of formula V, with complex hydrides, preferably lithium aluminum hydride in an alcohol such as ethanol, or sodium borohydride in the presence of LiCl in diglycol or LiAlH[OC(CH₃)₃]₃ in an ether such as tetrahydrofuran. Typical examples are 2-(2-methyl-[3]-piperidyl)ethanol, which can be obtained from 7a-methyl-2,3,3a,7a-tetrahydro-4H-furo[2,3-b]pyran (prepared from acrylaldehyd and 5-methyl-2,3-dihydrofuran) by reaction with an aqueous solution of hydrochloric acid, saturating the reaction solution with ammonia and subsequent hydrogenation with hydrogen on Raney nickel at 100° C./100 bar in the presence of minor amounts of aqueous sodium hydroxide (Bulletin de la Société Chimique de France, page 1139, 1142 (1954)), alternatively by heating ethyl (2-methyl-6-oxo-[4]piperidyl)acetate with lithium alanate in ether (Collections of Czechoslovak Chemical Communications 29, page 1582, 1587 (1964)), or by heating butyl (4-methyl-2,6-dioxo-[4]piperidyl)acetate with lithium alanate in dibutyl ether (Collections of Czechoslovak Chemical Communications 31, 4592 (1966)); 2-methyl-[3]piperidylmethanol, which can be obtained from ethyl 2-methyl-[3]piperidylcarboxylate (prepared from ethyl 3-amino-2-[2-cyanoethyl]crotonate by hydrogenation on nickel/fuller's earth in ethanol (Chemische Berichte 82, page 104 (1949)) or from ethyl 2-[2-cyanoethyl]acetate on Raney nickel in ethanol (J. Amer. Chem. Soc. 72, page 2594, 2596 (1950)) by reduction with complex hydrides; 4-methyl- or 5-methyl-[3]piperidyl methanol, which can be obtained by hydrogenation of diethyl 2-cyano-3-methylglutarate or diethyl 2-cyano-4-methylglutarate in ethanolic hydrogen chloride in the presence of platinum dioxide, reduction of the resultant 4- or 5-methyl-5-carbethoxy-2-piperidone by the method of Borch with NaBH₄ in the presence of Me₃OBF₄ in methylene chloride at temperatures below 10° C. to give ethyl 4- or 5-methyl-[3]-piperidylcarboxylate (Bull. Soc. Chim. France, page 663 (1986) (4)) and reduction thereof with complex hydrides; or 6-methyl-[3]-piperidyl methanol, which can be obtained by hydrolysis of 6-methyl-3-cyanopyridine with sulfuric acid in ethanol at reflux temperature, hydrogenation of the resultant ethyl 6-methyl-[3]pyridinecarboxylate in ethanol-saturated hydrogen chloride in the presence of platinum dioxide (Bull. Soc. Chim. France, page 663 (1986) (4)), and reduction of the resultant ethyl 6-methyl-[3]-piperidylcarboxylate with complex hydrides.

Besides these more general methods of synthesis, there are a number of further processes for the preparation of special compounds of formula I, a number of which are outlined below and which can be suitably carried out in general manner.

For example, 3-methylpiperidin-4-ol of formula V can be prepared from N-benzyl-3-methylpiperidin-4-ol by shaking with palladium/charcoal in ethanol with hydrogen (Can. J. Chem. 50, 803 (1972), or by reduction of 3-methyl-piperidin-4-one with sodium borohydride in the presence of potassium hydroxide in aqueous solution (Bull. Acad. Sci. USSR, Div. Chem. Sci. (English version), page 1788 (1965)); 2,5-dimethylpiperidin-4-ol of formel V can be prepared by reduction of 2,5-dimethylpiperidin-4-one with sodium in ethanol or hydrogen in the presence of a platinum catalyst (Bull. Acad. Sci. USSR, Div. Chem. Sci. (English version), page 65 (1954)); 4-methyl-3-hydroxymethylpiperidine of formula V can be prepared by aminomercuration of 2-aminomethyl-3-methyl-4-penten-1-ol with mercury acetate in tetrahydrofuran/water with subsequent reductive removal of the mercury radical with sodium borohydride (J. Het. Chem. 9, page 1081 (1972)); and 2,6-diethyl- or 2,6-dimethyl-3-hydroxymethylpiperidine can be prepared from N-[(1-ethyl- or 1-methyl-)-4-pentenyl]nitronene via the corresponding 2-endo,8-exo-diethyl- or 2-endo,8-exo-dimethyl-7-oxa-1-azabicyclo[3.2.1]octane with zinc dust in aqueous acetic acid to give the all-cis-form (J. Am. Chem. Soc. 111, 3363 (1989)).

The following process is especially preferred for the preparation of those compounds of formula V, wherein R₁" is a hydroxyl group and R₂" is a hydrogen atom, X₁ is an amino protective group, and the other substituents are as previously defined, with the proviso that at least one of the substituents R is bonded to the ring carbon atom adjacent to the piperidine ring nitrogen;

Firstly, a compound of formula XII,

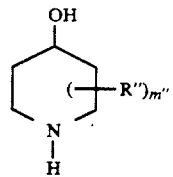

(XII)

wherein R" is C₁-C₂alkyl and m" is 0 or 1, is protected by an amino protective group described in process (a), conveniently by an acyl radical of a carbonic acid half-ester, preferably lower alkoxycarbonyl which is branched in 1-position of the lower alkyl moiety, typically tert-butoxycarbonyl, by reacting the compound of formula XII with an activated derivative of the carbonic acid half-ester, preferably an anhydride or an acid halide, e.g. di-tert-butyldicarbonate or tert-butyloxycarbonyl chloride, in an aprotic solvent such as a halogenated hydrocarbon, e.g. methylene chloride, in the temperature range from 20° C. to the reflux temperature of the reaction mixture, and, preferably afterwards, reacting the N-acylated product to introduce a hydroxyl protective group, as described hereinbelow, preferably a hydroxyl protective group which is removable under conditions different from those for removing the amino protective group, preferably 2-oxa- or 2-thiacycloalkyl containing 5–7 ring atoms, conveniently 2-tetrahydrofuryl or 2-tetrahydropyranyl, or a corresponding thia analog, as well as 1-phenyl-lower alkyl such as benzyl, diphenylmethyl or trityl, wherein the phenyl moieties may be substituted by halogen, e.g. chloro, lower alkoxy, e.g. methoxy, and/or nitro, conveniently by one of the methods described in the standard textbooks listed below, preferably in the case of 2-oxa- or 2-thiacycloalkyl by reacting a suitably mono-2-unsaturated 2-oxa- or 2-thiacycloalkyl compound, preferably 3,4-dihydro-2H-pyran, in an aprotic solvent, e.g. a halogenated hydrocarbon such as methylene chloride, in the presence of a weakly acid compound such as a pyridinium salt, conveniently pyridinium (toluene-4-sulfonate), in the temperature range from 0° to 50° C., preferably at room temperature, reacting the resultant compound of formula XIII,

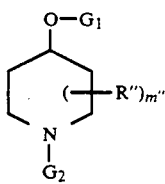 (XIII)

wherein $G_1$ is a hydroxy protective group and $G_2$ is an amino protective group as just described, and the other symbols have the meanings given for compounds of formula XII, with a lithium alkyl compound, e.g. sec-lower alkyllithium, conveniently sec-butyllithium, which is added preferably dissolved in a cyclic, a linear or a branched hydrocarbon or a mixture of such hydrocarbons, e.g. cyclohexane:isopentane, in the presence of a tertiary nitrogen base such as a mono- or di-(N,N-di-lower alkylamino)-lower alkane, e.g. N,N,N',N'-tetramethylethylenediamine, preferably under inert gas such as argon or nitrogen, in an aprotic solvent, preferably an ether such as diethyl ether, in the temperature range from 0° to −100° C., preferably from −60° to −80° C. The resultant lithiated compound is preferably reacted direct in situ, in the same solvent and under the same conditions as described for the lithiation, to introduce one $C_1$–$C_2$alkyl radical or, especially after isolation of the monoalkylated intermediate and the preparation of its lithiated derivative by the method just described, two $C_1$–$C_2$alkyl radicals, using a compound of formula XIV, $(C_1$–$C_2$-Alkyl$)$-Y (XIV), wherein Y is a nucleofugic leaving group, for example as described in process (b), e.g. sulfonyloxy carrying aliphatic or aromatic substituents, typically lower alkanesulfonyloxy, e.g. methanesulfonyloxy, or lower alkylphenylsulfonyloxy (=lower alkylphenyl-$SO_2$—O—), typically p-toluenesulfonyloxy, or preferably a halogen atom, e.g. a chlorine, bromine or, preferably, an iodine atom, and $C_1$–$C_2$alkyl is methyl or ethyl, or a di-($C_1$–$C_2$alkyl)sulfate, preferably dimethyl sulfate or diethyl sulfate, or methyl fluorosulfonate, to give a compound of formula XV

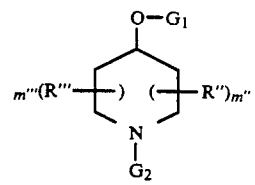 (XV)

wherein R''' is $C_1$–$C_2$alkyl and is in 2-, 6- or 2- and 6-position of the central piperidine ring, m''' is 1 or 2, and the other substituents have the given meanings, with the proviso that the sum of m'' and m''' is 1 or 2, then removing the hydroxy protective group $G_1$ from the compound of formula XV, preferably selectively, in the case of the 2-oxa- or 2-thiacycloalkyl protective groups containing 5–7 atoms, such as 2-tetrahydrofuryl or 2-tetrahydropyranyl or a corresponding thia analog, conveniently under mild acid conditions, as in the presence of a cationic exchanger in the H+form, preferably in an alcohol such as methanol or ethanol, in the temperature range from 0° to 60° C., typically at room temperature. The product obtained is a compound of formula XVI

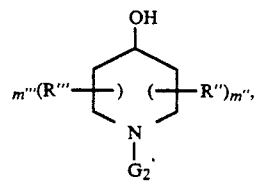 (XVI)

wherein the substituents are as just defined, and corresponds to a compound of formula V, wherein $R_1''$ is a hydroxy group and $R_2''$ is a hydrogen atom, $X_1$ is an amino protective group and the other substituents have the given meanings, with the proviso that at least one of the substituents R is bonded to the ring carbon atom adjacent to the piperidine ring nitrogen.

If desired, provided an isomer or a mixture of isomers of the compound of formula XVI is obtained in which the configuration at the carbon atom which carries the hydroxy group shall be subjected to an inversion, a corresponding 4-acyloxy derivative of the compound of formula XVI is prepared by an intramolecular dehydration reaction, preferably a variant of the Mitsunobo reaction (cf. Tetrahedron Lett. 32, 3017 (1991)), in which the compound of formula XVI is first reacted with an acidic carboxy compound, preferably an arylcarboxylic acid which is activated by electrophilic substituents, typically by 1 to 3 nitro, fluoro, chloro or bromo substituents, preferably m- or p-substituted benzoic acid, or a 2-halogenated lower alkanecarboxylic acid, e.g. 2,2,2-trichloro-or 2,2,2-trifluoroacetic acid, most preferably 4-nitrobenzoic acid, in the presence of a trairylphosphine, e.g. triphenylphosphine, and a diester of N,N'-azodicarboxylic acid, conveniently a di-lower alkyl ester of N,N'-azodicarboxylic acid, e.g. diethyl N,N'-azodicarboxylate, preferably in an aprotic solvent, typically an ether, e.g. a cyclic ether such as tetrahydrofuran or, preferably, an aromatic solvent such as benzene or toluene, preferably under an inert gas such as nitrogen, and in the preferred temperature range from 0° C. to 80° C., more particularly from 10° to 40° C., typically at 20° to 30° C. This reaction is preferably conducted such that, at the carbon atom carrying the hydroxy group, the acylated hydroxy group is introduced under inversion. The corresponding compound of formula XVI, in which the configuration at the carbon atom in 4-position undergoes inversion by converting the acyloxy group into a hydroxy group, is then prepared therefrom. This inversion is preferably effected selectively without removal of the amino protective group $G_2$, conveniently by base catalysis, e.g. by an alkali metal hydroxide such as potassium hydroxide or, preferably, by transesterification of the acyl radical in an alcohol such as methanol or ethanol, in the presence of catalytic amounts of an alkali metal alcoholate such as sodium or potassium methoxylate or sodium or potassium ethoxylate, in the temperature range from 0° to 60° C., typically at about room temperature.

Compounds of formula V, wherein $R_1''$ is a hydroxy group and $R_2''$ is a hydrogen atom, $X_1$ is an amino protective group, and the other substituents have the given meanings, with the proviso that at least one of the substituents R is bonded to the ring carbon atom adjacent to the piperidine ring nitrogen, can also be obtained by introducing an amino protective group into the corresponding compounds in which $X_1$ is hydrogen, conveniently in a manner substantially similar to that described above in connection with the introduction of the amino protective group $G_2$ into compounds of formula XII, to give likewise compounds of formula XVI as defined above.

Compounds of formula IV containing the above defined substituents can generally be obtained from compounds of formula V by converting the radical $R_1''$ or $R_2''$ in a compound of formula V into the radical $R_1'$ or $R_2'$, as described in connection with process (b).

As continuation of the particularly preferred process for the preparation of compounds of formula V, it is possible to react compounds of formula XVI in the same way as described in connection with compounds of formula V which carry a free hydroxyl group $W_1$ in process (b), to give the compounds of formula XVII falling under formula IV

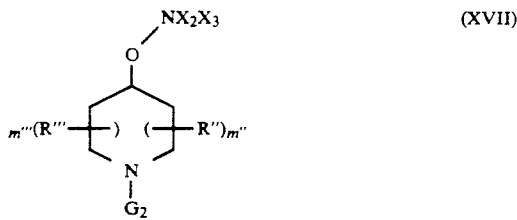

(XVII)

wherein $X_2$ and $X_3$ are as defined for compounds of formula IV in the radical $R_1'$ of formula IVa, and preferably together are a bisacyl radical, preferably unsubstituted phthalyl or phthalyl which is substituted by the same substituents as defined above in the definition of the protective groups in process (a) in connection with substituted benzoyl, typically the phthalyl radical which, together with the nitrogen atom to be protected, forms a 1H-isoindol-1,3(2H)-dione (phthalimido group), or lower alkyldicarboxylic acid radicals such as the succinic acid radical, lower alkenyldicarboxylic acid radicals such as the maleic acid radical, or $C_6$-$C_{12}$bicyclodicarboxylic acid radicals such as the 5-norbornene-2,3-dicarboxylic acid radical, and the other substituents are as defined for compounds of formula XVI. The removal of protective groups, especially under acid conditions, preferably with a mineral acid such as a hydrohalic acid, in the presence of absence of an organic solvent, e.g. an alcohol such as methanol, makes it possible to obtain compounds of formula I, wherein $R_1$ is the radical —O—$NH_2$, $R_2$ is a hydrogen atom, R is methyl or ethyl, at least one of the substituents R is bonded to the ring carbon atom adjacent to the piperidine ring nitrogen, and m is 1 or 2, or salts thereof, from the compounds of formula XVII.

General comments on the processes:

All the above process steps can be carried out under per se known reaction conditions, preferably those specifically mentioned, in the absence or, usually presence of solvents or diluents, preferably those which are inert to the reactants and dissolve them, in the absence or presence of catalysts, condensing agents or neutralising agents, e.g. ion exchangers such as cationic exchangers, typically in the H+ form, depending on the type of reaction and/or reactants at low, normal or elevated temperature, e.g. in the temperature range from about $-100°$ C. to about 190° C., preferably from about to $-80°$ C. to about 150° C., typically from $-80°$ C. to $-60°$ C., at room temperature, at $-20°$ C. to 40° C. or at the boiling point of the solvent used, under atmospheric pressure or in a closed reactor, under normal or elevated pressure, and/or in an inert atmosphere, e.g. in an argon or nitrogen atmosphere.

All starting materials and intermediates may be in salt form, provided salt-forming groups are present. Salts may also be present during the reaction of such compounds, provided the reaction is not thereby adversely affected.

In all reaction steps, mixtures of isomers can be separated into the individual isomers, typically diastereoisomers or enantiomers, or into any mixtures of isomers, typically racemates or mixtures of diastereoisomers, conveniently by the methods described under there heading "Additional process measures".

In specific cases, for example hydrogenation reactions, Mitsunobu reactions with inversions, or lithiations as described above, stereoselective reactions can be carried out so that it is easier to obtain individual isomers.

The solvents from which those suitable for the particular reaction can be selected include typically water, esters such as lower alkyl-lower alkanoates, e.g. diethyl acetates, ethers such as aliphatic ethers, e.g. diethyl ether, or cyclic ethers, e.g. tetrahydrofuran, liquid aromatic hydrocarbons such as benzene or toluene, alcohols such as methanol, ethanol or 1- or 2-propanol, nitriles such as acetonitrile, halogened hydrocarbons such as methylene chloride, acid amides such as dimethyl formamide, bases such as heterocyclic nitrogen bases, e.g. pyridine, carboxylic acid anhydrides such as lower alkanoic acid anhydrides, e.g. acetic anhydride, cyclic, linear or branched hydrocarbons such as cyclohexane, hexane or isopentane, or mixtures of these solvents, e.g. aqueous solutions, provided not otherwise stated in the description of the processes. Such mixtures of solvents can also be used in the working up, typically by chromatography or distribution.

Functional groups in starting materials and the intermediates which shall not participate in the particular reaction, especially amino groups (e.g. the piperidine nitrogen or the aminooxy nitrogen), or hydroxy groups (if, for example, groups analogous to $W_1$ or $W_2$ in precursors of compounds of formula V are hydroxy) can be protected by suitable protective groups (conventional protective groups) which are normally used in the synthesis of peptides, as well as of cephalosporins and penicillins as well as nucleic derivatives and sugars. These protective groups may already be present in the precursors and are designed to protect the functional groups in question against undesirable side-reactions such as acylations, etherifications, esterifications, oxidations, solvolyses and the like. In specific cases the protective groups can also effect a selective, typically stereoselective, reaction course. Characteristic of protective groups is that they are easily removable, i.e. without undesirable side-reactions, typically by solvolysis, reduction, photolysis or also by enzymatic methods, e.g. also under physiological conditions. Within the scope of this invention, only those groups are designated as protective groups that are not present in the final products.

The protection of functional groups by such protective groups, the protective groups themselves and reactions to remove them are described in standard works such as J. F. W. McOmie, "Protective Groups in Organic Chemistry", Plenum Press, London and New York 1973, in Th. W. Greene, "Protective Groups in Organic Synthesis", Wiley, New York 1981, in "The Peptides"; Volume 3 (E. Gross and J. Meienhofer, ed.) Academic Press, London and New York 1981, in "Methoden der organischen Chemie" Methods of Organic Chemistry), Houben-Weyl, 4th edition, Vol. 15/I, Georg Thieme Verlag, Stuttgart 1974, in H. -D. Jakubke and H. Jescheit, "Aminosäuren, Peptide, Proteine" (Amino acids, Peptides, Proteins) Verlag Chemie, Weinheim, Deerfield Beach and Basel 1982, and in Jochen Lehmann, "Chemie der Kohlenhydrate: Monosaccharide und Derivate" (Chemistry of Hydrocarbons: Monosaccharides and Derivatives), Georg Thieme Verlag, Stuttgart 1974.

Amino groups are preferably protected as described in process (a). Preferred conditions for removing the amino protective groups will also be found therein.

A hydroxy group may be protected by an acyl group, typically by halogen such as chloro, substituted lower alkanoyl such as 2,2-dichloroacetyl, or, preferably, by an acyl radical of a carbonic acid half-ester suitable for protected amino groups, or unsubstituted or substituted benzoyl. A hydroxy group can also be protected by tri-lower alkylsilyl, including trimethylsilyl, triisopropylsilyl and tert-butyl-dimethylsilyl, a readily removable aliphatic etherifying group, typically an alkyl group such as tert-lower alkyl, e.g. tert-butyl, an oxa- or a thiaaliphatic or thiacycloaliphatic, preferably a 2-oxa- or 2-thiaaliphatic or 2-oxa- or 2-thiacycloaliphatic hydrocarbon radical, for example 1-lower alkoxy-lower alkyl or 1-lower alkylthio-lower alkyl, e.g. methoxymethyl, 1-methoxyethyl, 1-ethoxyethyl, methylthiomethyl, 1-methylthioethyl or 1-ethylthioethyl, or 2-oxa- or 2-thiacycloalkyl containing 5-7 ring atoms, e.g. 2-tetrahydrofuryl or 2-tetrahydropyranyl, or a corresponding thia analog, as well as 1-phenyl-lower alkyl such as benzyl, diphenylmethyl or trityl, wherein the phenyl moieties may be substituted by halogen, e.g. chloro, lower alkoxy, e.g. methoxy, and/or nitro. A preferred hydroxy protective group is typically 2,2,2-trichloroethoxycarbonyl, 4-nitrobenzyloxycarbonyl, 4-nitrobenzoyl, diphenylmethoxycarbonyl, tetrahydropyran-2-yl or trityl.

The removal of the protective groups that are not a constituent of the desired final product of formula I, typically the amino and/or hydroxy protective groups, is effected in a manner known per se, conveniently by solvolysis, preferably hydrolysis, alcoholysis or acidolysis, or by reduction, preferably hydrogenolysis or chemical reduction, as well as photolysis, if appropriate stepwise or simultaneously, while enzymatic methods can also be used. The removal of the protective groups is described in the standard textbooks listed in the section dealing with "protective groups".

A hydroxy group protected by a suitable acyl group, a tri-lower alkylsilyl group or by unsubstituted or substituted 1-phenyl-lower alkyl, is set free in substantially the same way as a correspondingly protected amino group. For example, a hydroxy group protected by 2,2-dichloroacetyl may be set free by basic hydrolysis, a hydroxy group protected by tert-lower alkyl or by a 2-oxa- or 2-thiacliphatic or 2-oxa-or 2-thiacycloaliphatic hydrocarbon radical by acidolysis, e.g. by treatment with a mineral acid or a strong carboxylic acid, e.g. trifluoroacetic acid, or in in the presence of a cationic exchanger in the H+ form, a hydroxy group protected by unsubstituted or substituted benzoyl, e.g. 4-nitrobenzoyl, by alcoholysis, conveniently methanolysis, preferably in the presence of a catalytic amount of an alkali metal alcoholate, e.g. sodium methylate (sodium methanolate).

In the process of this invention it is preferred to use those starting materials which result in the compounds initially described as especially useful.

The invention also relates to those embodiments of the process in which a compound obtainable as intermediate in any stage of the process is used as starting material, or the process is discontinued in any step, or in which a starting material is formed under the reaction conditions or used in the form of a derivative, conveniently a salt thereof.

Salts of intermediates that carry at least one basic group, typically appropriate compounds of formula IV or V, are acid addition salts, for example as described above in connection with salts of compounds of formula I. Where intermediates carry protective groups with negatively charged substituents, salts with bases can also be formed, and also mixed salts or inner salts.

Novel starting materials and/or intermediates, preferably those of formula IV, are also an object of the present invention. It is preferred to use those starting materials and to choose those reaction conditions that lead to the compounds cited in this specification as being particularly preferred.

Preferred intermediates are those of formula IV above, wherein either $R_1'$ is a radical of the formula IVa,

$$-(CH_2)_n-O-NX_2X_3 \qquad (IVa),$$

wherein n is 0 or 1, and $R_2'$ is hydrogen, or $R_1'$ is hydrogen and $R_2'$ a radical of formula IVb

$$-(CH_2)_p-O-NX_2X_3 \qquad (IVb),$$

wherein p is 1 or 2, and the other symbols are as defined for the compound of formula I, and $X_1$, $X_2$ and $X_3$ are each independently of one another an amino protective group or hydrogen, with the proviso that at least one of the groups $X_1$, $X_2$ and $X_3$ is an amino protective group, or wherein $X_1$ is an amino protective group or hydrogen, and $X_2$, together with $X_3$, form a bivalent amino protective group, or salts thereof, provided salt-forming groups are present.

More preferred intermediates of formula IV are those wherein $X_1$ is hydrogen or an amino protective group, $R_1'$ is a radical of formula IVa as indicated in claim 18, wherein n is 0 and $X_2$ and $X_3$ are hydrogen or, when taken together, form a bivalent amino protective group, $R_2'$ is hydrogen, R is $C_1$–$C_2$alkyl, and m is 1 or 2, and R is bonded only to that carbon atom which is attached direct to the nitrogen hetero atom of the central piperidine ring system, or salts thereof, provided salt-forming groups are present.

A compound of formula IV is most preferred wherein $X_1$ is hydrogen or tert-butoxycarbonyl, $R_1'$ is —O—$NH_2$ or —O—$NX_2'X_3'$, wherein $X_2'$ and $X_3'$, together with the linking nitrogen atom, form a 1H-isoindol-1.3(2H)-dionyl radical, R is methyl or ethyl, and m is 1 or 2, or salts thereof, provided salt-forming groups are present, those compounds being most especially preferred in which the substituent R or substituents R are in trans-position relative to $R_1'$.

The invention relates most particularly to the compounds, novel intermediates and processes described in the Examples.

Pharmaceutical compositions

The present invention also relates to pharmaceutical compositions which contain as active compound one of the pharmacologically active compounds of formula I or a pharmaceutically acceptable salt thereof. Especially preferred are those for enteral, preferably oral, administration, and also for parenteral administration. the compositions contain the active compound alone or preferably together with a pharmaceutically acceptable carrier. The dosage will depend on the disease to be treated, and on the species, age, weight, skin area and individual condition of the patient as well as on the mode of administration.

The pharmaceutical compositions contain from about 5% to about 95% of the active compound, whereas compositions in single unit dosage form preferably contain from about 20 to about 90%, and compositions not in single unit dosage form preferably contain about 5% to about 20%, of the active compound. Dosage unit forms such as dragées, tablets or capsules contain from 0.01 g to about 2 g, preferably from about 0.05 g to about 1.0 g of active compound, preferably from 0.1 to 0.6 g.

The present invention also relates to the use of compounds of formula I (and, where appropriate, of formula IV as pro-drug) for the preparation of pharmaceutical compositions for use as ODC inhibitors, typically for the treatment of diseases that respond to the inhibition of ODC, especially the above mentioned diseases.

The pharmaceutical compositions of this invention are prepared in a manner known per se, typically by conventional mixing, granulating, confectioning, dissolving or lyophilising methods. Thus pharmaceutical compositions for oral administration can be obtained by combining the active compound with one or more than one solid carrier, optionally granulating a mixture so obtained, and, if desired, processing the mixture or granulate to tablets or dragée cores, with or without the addition of further excipients.

Suitable carriers are especially fillers such as sugars, conveniently lactose, saccharose, mannitol or sorbitol, cellulose preparations and/or calcium phosphates, typically tricalcium phosphate or calcium hydrogen phosphate, and also binders such as starch pastes, conveniently maize, corn, rice or potato starch, methyl cellulose, hydroxymethylpropyl cellulose, sodium carboxymethyl cellulose and/or polyvinyl pyrrolidone, and/or, if desired, disintegrators such as the above-mentioned starches, also carboxymethyl starch, crosslinked polyvinylpyrrolidone, alginic acid or a salt thereof such as sodium alginate. Further excipients are in particular flow control agents and lubricants, typically silica, talcum, stearic acid or salts thereof such as magnesium stearate or calcium stearate, and/or polyethylene glycol or derivatives thereof.

Dragée cores can be provided with suitable non-enteric or enteric coatings, typically using concentrated sugar solutions which may contain gum arabic, talcum, polyvinylpyrrolidone, polyethylene glycol and/or titanium dioxide, shellac solutions in suitable organic solvents or mixtures of solvents or, for the preparation of enteric coatings, solutions of suitable cellulose preparations such as acetyl cellulose phthalate or hydroxypropyl methyl cellulose phthalate. Dyes or pigments can be added to the tablets or dragée coatings, conveniently to identify or indicate different doses of active compound.

Further pharmaceutical compositions for oral administration are dry-filled capsules made of gelatin and also soft-sealed capsules consisting of gelatin and a plasticiser such as glycerol or sorbitol. The dry-filled capsules can contain the active ingredient in the form of granules, conveniently in admixture with fillers such as lactose, binders such as starches, and/or glidants such as talcum or magnesium stearate, and with or without stabilisers. In soft capsules, the active ingredient is preferably dissolved or suspended in a suitable liquid, typically a fatty oil, paraffin oil or a liquid polyethylene glycol, to which a stabiliser can also be added.

Further oral dosage forms are typically syrups prepared in conventional manner that contain the active compound, for example in suspended form and in a concentration of c. 5% to 20%, preferably from c. 10% or in a similar concentration, which gives a suitable individual dose when measured in an amount of 5 or 10 ml. Also suitable are powdered or liquid concentrates for preparing shakes, conveniently in milk. Such concentrates can also be packed in single dose formulations.

Suitable pharmaceutical compositions for rectal administration are typically suppositories, which consist of a combination of the active compound with a suppository base. Suitable suppository bases are, for example, natural or synthetic triglycerides, paraffin hydrocarbons, polyethylene glycols and higher alkanols.

Particularly suitable compositions for parenteral administration are aqueous solutions of the active compound in water-soluble form, typically of a water-soluble salt, or aqueous injection suspensions which contain viscosity increasing substances such as sodium carboxymethyl cellulose, sorbitol and/or dextran, with or without stabilisers. In these cases, the active compound can also exist in the form of a lyophilisate, without or together with excipients, and can be dissolved by the addition of appropriate solvents before the parenteral administration.

The solutions used for parenteral administration can also be used as infusion solutions.

The invention also relates to a method of treating the above mentioned conditions in warm-blooded animals, i.e. mammals and, in particular, humans, preferably those warm-blooded animals in need of such treatment. The compounds of formula I or also pro-drugs, especially of formula IV, and the pharmaceutical salts thereof, provided salt-forming salts are present, are administered prophylactically or therapeutically, conveniently in a dose effective for inhibiting ornithin decarboxylase, to treat one of the cited diseases, typically tumours or protozoa infections. The contemplated daily dose for administration to a patient of approximately 70 kg body weight will normally be from about 0.3 g to about 15 g, preferably from about 0.5 g to about 5 g, of a compound of this invention.

The pharmaceutical compositions are preferably those which are suitable for administration to a warm-blooded animal, for example a human being, for the therapy or prophylaxis of one of the above mentioned diseases which respond to an inhibition of ornithin decarboxylase, and which comprise an effective amount of a compound of formula I, or a pharmaceutically acceptable salt thereof, for inhibiting this enzyme, preferably in conjunction with at least one carrier.

The following Examples illustrate the invention without restricting the scope thereof. Temperatures are given in Celsius degrees. The following abbreviations are used: BOC $\triangleq$ tert-butyloxycarbonyl; $R_f \triangleq$ ratio of the distance travelled to the solvent front in thin-layer chromatography; mp $\triangleq$ melting point; brine $\triangleq$ saturated solution of sodium chloride; decomp. $\triangleq$ with decomposition. In mixtures of solvents, diluents and eluants, the parts by volume of solvent are indicated in each mixture (v:v).

EXAMPLE 1 trans-2-Methyl-4-aminooxypiperidine sulfate

With stirring, a mixture of 16.54 g (0.0472 mol) of 2-(trans-N-BOC-2-methyl-4-piperidyloxy)-1H-isoindol-1,3(2H)-dione in 45 ml of water and 30 ml of concentrated hydrochloric acid is heated for 2 hours under reflux, to give initially a solution from which after a short time a crystalline product (phthalic acid) precipitates. The reaction mixture is filtered after cooling to 0° C. The filter residue is washed with water and the filtrate is concentrated by evaporation under vacuum. The residue is taken up in ethanol and evaporated to dryness under vacuum. The residue is taken up again in ethanol and concentrated by evaporation under vacuum, giving crude trans-2-methyl-4-aminooxy-piperidine dihydrochloride as resinous residue. The residue is dissolved in 30 ml of brine, a small amount of undissolved solids are removed by filtration and the filtrate is neutralised with 20 ml of 30% aqueous sodium hydroxide. After thorough extraction with methylene chloride (2 portions of 100 ml and 2 portions of 50 ml), the combined organic organic phase is dried over sodium sulfate and concentrated by evaporation under vacuum, giving trans-2-methyl-4-aminooxy-piperidine as an oily residue which is dissolved in 100 ml of ethanol. After addition of 42.6 ml of 2N sulfuric acid, the crystallised product is isolated by filtration, washed with ethanol and ether and dried at 100° C. under a high vacuum. The title compound melts at 251°–253° C. (decomp.).

The starting materials are prepared as follows:

a) 2-(trans-N-BOC-2-methyl-4-piperidyloxy)-1H-isoindol-1,3(2H)-dione.

With stirring and under nitrogen, a solution of 19.68 g (0.1177 mol) of diethyl azodicarboxylate (93%) in 70 ml of benzene is added dropwise at 20°–30° C. to a suspension of 25.2 g (0.117 mol) of cis-N-BOC-2-methyl-4-hydroxy-piperidine, 19.1 g (0.117 mol) of N-hydroxyphthalimide and 30.7 g (0.117 mol) of triphenylphosphine in 310 ml of benzene. The reaction mixture is further stirred for 2¼ hours at room temperature, cooled to 5° C., and precipitated diethyl ester of 1,2-hydrazinedicarboxylic acid is removed by filtration. The filtrate is concentrated by evaporation under vacuum and the residue is dissolved in 500 ml of ether and then cooled again to 5° C. Precipitated triphenylphosphine oxide is removed by filtration and the filtrate is concentrated by evaporation under vacuum. The resinous residue is purified by flash chromatography over silica gel (granular size 0.04–0.063 mm) using ethyl acetate/hexane (3:1). For complete purification, the still slightly impure product is subjected once more to flash chromatography over silica gel eluted with ethyl acetate/hexane mixtures (1:3, 1:2 and 1:1). The fractions containing the product are concentrated to give the title compound as a colourless resin; $R_f=0.65$ (silica gel/ethyl acetate:hexane (2:1)).

b) cis-N-BOC-2-methyl-4-hydroxypiperidine

A solution of 14.6 g (0.04876 mol) of cis-N-BOC-2-methyl-4-[(tetrahydropyran-2-yl)oxy]piperidine in 120 ml of methanol is treated with 20 g of cationic exchanger Dowex ® 50 WX8 (H+ form; 50–100 mesh (50 mesh corresponds to a granular size of c. 300 μm, 100 mesh to c. 150 μm); cationic exchanger based on a styrene/divinylbenzene polymer containing sulfonyl groups; registered trademark of Dow Chemicals Co., USA)), and the mixture is stirred for 22 hours at room temperature. After filtration, washing the ion exchanger with methanol and concentrating the filtrate under vacuum, the title compound is obtained in the form of a viscous oil, $R_f=0.16$ (silica gel/ethyl acetate:hexane (1:2)).

c) cis-N-BOC-2-methyl-4-[(tetrahydropyran-2-yl)oxy]piperidine 19.83 ml (0.132 mol) of N,N,N'N'-tetramethylethylenediamine and then 55.55 ml of a 1.3 molar solution of sec-butyllithium (0.0722 mol) in cyclohexane:isopentane (92:8) are added dropwise at −65° to −70° C. under nitrogen to a solution of 17.4 g (0.06 mol) of N-BOC-4-[(tetrahydropyran-2-yl)oxy]piperidine in 120 ml of ether. The reaction mixture is stirred for 3.5 hours at −70° C. and then a solution of 4.5 ml (0.07228 mol) of methyl iodide in 100 ml of ether is added dropwise over c. 15 minutes, whereupon the temperature of the reaction mixture rises to a maximum of −60° C. The reaction mixture is further stirred for 5 minutes at −60° C., then the cooling bath is removed and the temperature is allowed to rise to 20° C. Afterwards 120 ml of water are added dropwise to the reaction mixture, with stirring. The organic phase is separated and extracted with 3×75 ml of ether. After washing with brine and drying over sodium sulfate, the combined ether phases are concentrated under vacuum and the oily residue is purified by flash chromatography over silica gel/ethyl acetate:hexane (1:5). The fractions containing the product are concentrated, giving the title compound as a colourless oil; $R_f=0.49$ (silica gel/ethyl acetate:hexane (1:2)).

d) N-BOC-4-[(tetrahydropyran-2-yl)oxy]piperidine

With stirring, 8.16 ml (0.09 mol) of 3,4-dihydro-2H-pyran and 1.5 g (0.006 mol) of pyridinium-(toluene-4-sulfonate) are added to a solution of 12.08 g (0.06 mol) of N-BOC-4-hydroxypiperidine (cf. EP 0 278 621) in 300 ml of methylene chloride. The reaction mixture is stirred for 2.5 hours at room temperature, then washed with 2×50 ml of brine:water (1:1) mixture, dried over sodium sulfate and concentrated under vacuum, giving the title compound in the form of a colourless oil; $R_f=0.58$ (silica gel/ethyl acetate:hexane (2:1), which gradually solidifies in crystalline form at 0° C.

EXAMPLE 2 cis-2-Methyl-4-aminooxypiperidine sulfate

With stirring, a mixture of 0.69 g (0.00197 mol) of 2-(cis-N-BOC-2-methyl-4-piperidyloxy)-1H-isoindol-1,3(2H)-dione in 3 ml of water and 2 ml of concentrated hydrochloric acid is heated for 2.5 hours at reflux temperature and worked up as described in Example 1, affording the title compound which melts at 250°-251° C. (decomp.).

The starting compounds are prepared as follows:

a) 2-(cis-N-BOC-2-methyl-4-piperidyloxy)-1H-isoindol-1,3(2H)-dione A mixture of 0.65 g (0.00247 mol) of trans-N-BOC-2-methyl-4-hydroxypiperidine, 0.403 g (0.00247 mol) of N-hydroxyphthalimide and 0.648 g (0.00247 mol) of triphenylphosphine in 10 ml benzene is reacted in accordance with Example 1a with a solution of 0.434 ml (0.00256 mol) of diethyl azodicarboxylate (93%) in 2 ml of benzene. After filtration to remove diethyl 1,2-hydrazinedicarboxylate, the filtrate is concentrated under vacuum and the oily residue is purified by flash chromatography over silica gel using ethyl acetate:hexane (1:3), affording the title compound as a colourless resin; $R_f=0.53$ (silica gel/ethyl acetate:hexane (1:1).

b) trans-N-BOC-2-methyl-4-hydroxypiperidine

A mixture of 0.9 g (0.00246 mol) of trans-N-BOC-2-methyl-4-(4-nitrobenzoyloxy)piperidne, 12 ml of methanol and 0.022 ml of (0.000119 mol) of a 30% solution of sodium methylate in methanol is stirred for 15 hours at room temperature. The reaction mixture is filtered, the filtrate is concentrated under vacuum, and the residue is purified by flash chromatography over silica gel using ethyl acetate:hexane mixtures (1:2 and 1:1). Concentration of the fractions by evaporation gives the title compound in the form of a colourless oil; $R_f=0.59$ (silica gel/etyl acetate:hexane (1:2).

c) trans-N-BOC-2-methyl-4-(4-nitrobenzoyloxy)-piperidine

With stirring, a solution of 2 ml (0.012 mol) of diethyl azodicarboxylate (93%) in 10 ml of toluene is added dropwise at 5°-10° C. to a suspension of 2.15 g (0.01 mol) of cis-N-BOC-2-methyl-4-hydroxypiperidine (cf. Example 1b), 2.0 g (0.012 mol) of 4-nitrobenzoic acid and 3.15 g (0.012 mol) of triphenylphosphine in 30 ml of toluene. The reaction mixture is further stirred for 15 hours at room temperature and then filtered to remove precipitated diethyl hydrazinedicarboxylate. The filtrate is then concentrated under vacuum and the oily residue is purified by flash chromatography over silica gel using ethyl acetate:hexane (1:5). Concentration of the fractions containing the product gives the title compound as a crystalline residue which melts at 106°-108° C.

EXAMPLE 3 trans-2-Ethyl-4-aminooxypiperidine dihydrochloride

A mixture of 0.217 g (0.0005795 mol) of 2-(trans-N-BOC-2-ethyl-4-piperidyloxy)-1H-isoindol-1,3(2H)-dione, 3 ml of water and 2 ml of concentrated hydrochloric acid is reacted in accordance with the general procedure of Example 1. When concentrated with ethanol, the title compound precipitates in crystalline form. After recrystallisation from ethanol the product melts at 206°-207° C. (decomp.).

The starting materials are prepared as follows:

a) 2-(trans-N-BOC-2-ethyl-4-piperidyloxy)-1H-isoindol-1,3(2H)-dione

With stirring and under nitrogen, a solution of 0.283 ml (0.001693 mol) of diethyl azodicarboxylate (93%) in 1 ml of benzene is added dropwise at 20°-30° C. to a suspension of 0.37 g (0.001613 mol) of cis-N-BOC-2-ethyl-4-hydroxypiperidine, 0.263 g (0.001613 mol) of N-hydroxyphthalimide and 0.423 g (0.001613 mol) of triphenylphosphine in 5 ml of benzene. The reaction mixture is further stirred for 15 hours at room temperature, then filtered to remove precipitated diethyl 1,2-hydrazinedicarboxylate, and the filtrate is concentrated under vacuum. The residue is purified by flash chromatography over silica gel using ethyl acetate:hexane (1:3), to give the title compound as a colourless resin; $R_f=0.66$ (silica gel/ethyl acetate:hexane (2:1)).

b) cis-N-BOC-2-ethyl-4-hydroxypiperidine and trans-N-BOC-2-ethyl-4-hydroxypiperidine A mixture of 2.5 g (0.00798 mol) of N-BOC-2-ethyl-4-[(tetrahydropyran-2-yl)oxy]piperidine (cis/trans-mixture), 25 ml of methanol and 3.5 g of cationic exchanger Dowex® 50 WX8 (H+ form; 50-100 mesh (50 mesh corresponds to a granular size of c. 300 μm, and 100 mesh to c. 150 μm); cationic exchanger based on a styrene/divinylbenzene polymer containing sulfonyl groups; registered trademark of Dow Chemical Co., USA) is stirred for 15 hours at room temperature. After filtration, washing the ion exchanger with methanol and concentrating the filtrate under vacuum, the oily residue is purified by flash chromatography over silica gel using ethyl acetate:hexane mixtures (1:3 and 1:2). The fractions containing the product are concentrated by evaporation to give the title compound, $R_f=0.17$, and the trans-compound, $R_f=0.12$ (silica gel/ethyl acetate:hexane (1:2)), each as an oil.

c) N-BOC-2-ethyl-4-[(tetrahydropyran-2-yl)oxy]-piperidine

Following the general procedure of Example 1c, a solution of 8.75 g (0.03 mol) of N-BOC-4-[tetrahydropyran-2-yl)oxy]piperidine (cf. Example 1d) in 60 ml of ether is reacted with 9.92 ml (0.066 mol) of N,N,N',N'-tetramethylethylenediamine and 27.78 ml (0.0361 mol) of a 1.3 molar solution of sec-butyllithium in cyclohexane:isopentane (92:8) and a solution of 2.92 ml (0.03614 mol) of ethyl iodide in 50 ml of ether. The crude product is purified by flash chromatography over silica gel using ethyl acetate:hexane mixtures (1:6 and 1:5) to give a cis/trans-mixture of the title compound in the form of a colourless oil; $R_f=0.39$ (silica gel/ethyl acetate:hexane (1:3)).

EXAMPLE 4 cis-2-Ethyl-4-aminooxypiperidine sulfate

A mixture of 0.85 g (0.00227 mol) of 2-(cis-N-BOC-2-ethyl-4-piperidyloxy)-1H-isoindol-1,3(2H)-dione, 6 ml of water and 4 ml of concentrated hydrochloride acid is reacted in accordance with the general procedure of Example 1. The crude resinous dihydrochloride of the title compound is converted as described in Example 1 into the crystalline sulfate which melts at 234°-235° C. (decomp.).

The starting material is prepared as follows:

a) 2-(cis-N-BOC-2-ethyl-4-piperidyloxy)-1H-isoindol-1,3(2H)-dione

A suspension of 0.74 g (0.003227 mol) of trans-N-BOC-2-ethyl-4-hydroxypiperidine (cf. Example 3b), 0.526 g (0.003227 mol) of N-hydroxyphthalimide and 0.846 g (0.003227 mol) of triphenylphosphine in 10 ml of benzene is reacted in accordance with the general procedure of Example 3a with a solution of 0.566 ml (0.003385 mol) of diethyl azodicarboxylate (93%) in 2 ml of benzene, to give the title compound as a colourless resin; $R_f=0.60$ (silica gel/ethyl acetate:hexane (2:1)).

EXAMPLE 5

2t,6t-Dimethyl-4r-aminooxypiperidine dihydrochloride

A mixture of 2.0 g (0.00534 mol) of 2-[N-BOC-(2t,6t-dimethyl)-4r-piperidyloxy]-1H-isoindol-1,3(2H)-dione, 10 ml of water and 8.5 ml of concentrated hydrochloric acid is reacted in accordance with the general procedure of Example 1. The crude dihydrochloride of the title compound is purified by crystallisation from methanol/ether, mp 211° C. (decomp.).

The starting materials are prepared as follows:

a) 2-[N-BOC-(2t,6t-dimethyl-4r-piperidyloxy]-1H-isoindol-1,3(2H)-dione

Following the general procedure of Example 3a, a suspension of 6.0 g (0.02616 mol) of N-BOC-2c,6c-dimethyl-4r-hydroxypiperidine, 4.27 g (0.02616 mol) of N-hydroxyphthalimide and 6.86 g (0.02616 mol) of triphenylphosphine in 50 ml of benzene is reacted with a solution of 4.6 ml (0.0275 mol) of diethyl azodicarboxylate (93%) in 15 ml of benzene. The crude product is purified by flash chromatography over silica gel using ethyl acetate:hexane mixtures (1:4 and 1:2) to give the title compound as a colourless resin which gradually solidifies in crystalline form, mp 107°–109° C.

b) N-BOC-2c,6c-dimethyl-4r-hydroxypiperidine

A mixture of 3.6 g (0.02786 mol) 2c,6c-dimethyl-4r-hydroxypiperidine [cf. J. Org. Chem. 15, 337–342 (1950) and Beilstein, 21, EIII/IV, 112], 6.7 g (0.03069 mol) of di-tert-butyldicarbonate and 40 ml of methylene chloride is heated for 24 hours under reflux and subsequently left to stand for 65 hours at 20° C. A second portion of 6.7 g (0.03069 mol) of di-tert-butyldicarbonate is added to the reaction mixture, which is again heated for 24 hours under reflux. The reaction is then concentrated by evaporation under vacuum and the oily residue is purified by flash chromatography over silica gel using ethyl acetate:hexane mixtures (1:4 and 1:1). Concentration of the fractions containing the product by evaporation gives the title compound as a colourless oil; $R_f=0.32$ (silica gel/ethyl acetate:hexane (1:1)).

EXAMPLE 6

Capsules

Capsules containing 0.25 g of active compound, e.g. one of the compounds of Examples 1–5, can be prepared as follows:

| Composition (for 5000 capsules) | |
|---|---|
| active compound | 1250 g |
| talcum | 180 g |
| corn starch | 120 g |
| magnesium stearate | 80 g |
| lactose | 20 g |

The powdered substances are forced through a sieve with a mesh size of 0.6 mm and mixed. 0.33 g portions of the mixture are filled into gelatin capsules on a capsule filling machine.

What is claimed is:

1. A compound of formula I

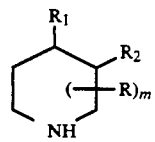

wherein either $R_1$ is a radical of formula Ia,

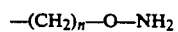

in which n is 0 or 1, and $R_2$ is hydrogen and $R_2$ is a radical of formula Ib,

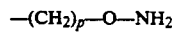

in which p is 1 or 2, and wherein R is $C_1$-$C_2$alkyl which is bonded to a carbon atom of the central piperidine ring system, but not to the same carbon atom as $R_1$ of formula Ia or as $R_2$ of formula Ib; and m is 1 or 2, or a salt thereof.

2. A compound according to claim 1 of the formula

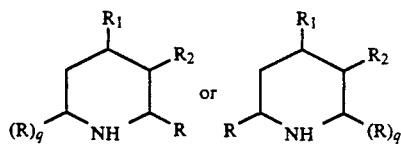

wherein q is 0 or 1, or a pharmaceutically acceptable salt thereof.

3. A compound of formula I according to claim 1, wherein n is 0 when $R_1$ is defined as the radical of formula Ia, or p is 1 when $R_2$ is defined as the radical of formula Ib, and the other symbols are as defined in claim 1, or a pharmaceutically acceptable salt thereof.

4. A compound of formula I according to claim 2, wherein n is 0 when $R_1$ is defined as the radical of formula Ia, or p is 1 when $R_2$ is defined as the radical of formula Ib, and the other symbols are as defined in claim 2.

5. A compound according to claim 1 of formula II

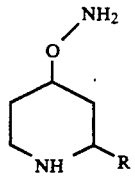

wherein R is $C_1$-$C_2$alkyl, or a pharmaceutically acceptable salt thereof.

6. A compound of formula II according to claim 5, wherein the —O—$NH_2$ radical and the substituent R which is $C_1$-$C_2$alkyl, are bonded to the central piperidine ring system in trans-position relative to each other, or a pharmaceutically acceptable salt thereof.

7. A compound of formula II according to claim 5, wherein R is methyl and is bonded to the central piperidine ring system in trans-position relative to the —O—$NH_2$ radical, or a pharmaceutically acceptable salt thereof.

8. A compound according to claim 1 of formula III

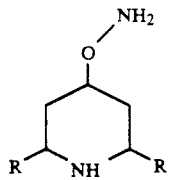 (III)

wherein the substituents R are each independently of the other $C_1$–$C_2$alkyl, or a pharmaceutically acceptable salt thereof.

9. A compound of formula III according to claim 8, wherein R is methyl and both substituents R are bonded to the central piperidine ring system in cis-position relative to each other, but in trans-position to the —O—NH$_2$ radical, or a pharmaceutically acceptable salt thereof.

10. A compound of formula I according to claim 1, selected from the group consisting of trans-2-methyl-4-aminooxypiperidine, cis-2-methyl-4-aminooxypiperidine, trans-2-ethyl-4-aminooxypiperidine, cis-2-ethyl-4-aminooxypiperidine and 2t,6t-dimethyl-4r-aminooxypiperidine, or a pharmaceutically acceptable salt thereof.

11. A pharmaceutical composition suitable for administration to a warm-blooded animal comprises an ornithine decarboxylase inhibiting amount of a compound of formula I according to claim 1 or a pharmaceutically acceptable salt thereof and a pharmaceutically acceptable carrier.

* * * * *